United States Patent [19]

Pirzada et al.

[11] Patent Number: 5,788,738
[45] Date of Patent: Aug. 4, 1998

[54] METHOD OF PRODUCING NANOSCALE POWDERS BY QUENCHING OF VAPORS

[75] Inventors: Shahid Pirzada; Tapesh Yadav, both of Tucson, Ariz.

[73] Assignee: Nanomaterials Research Corporation, Tucson, Ariz.

[21] Appl. No.: 707,341

[22] Filed: Sep. 3, 1996

[51] Int. Cl.⁶ .................................................. B22F 9/12
[52] U.S. Cl. ........................... 75/331; 164/46; 264/12
[58] Field of Search ........................... 75/331, 338, 345; 164/46, 463; 239/8; 264/12

[56] References Cited

U.S. PATENT DOCUMENTS

| | | | |
|---|---|---|---|
| 4,534,917 | 8/1985 | Walz | 75/338 |
| 4,619,845 | 10/1986 | Ayers et al. | 239/8 |
| 5,403,375 | 4/1995 | Konig et al. | 75/255 |
| 5,407,458 | 4/1995 | Konig et al. | 75/255 |

OTHER PUBLICATIONS

Jacobson et al., "Rapid Solidification Processing," Mat. Sci. and Eng., R11, 335 (1994).
R. Uyeda, "Studies of Ultrafinie Particles in . . . ," Prog. Mater. Sci., 35, 1 (1991).
R. W. Siegel, Materials Science and Technology, 15, VCH, Weinhem, 583 (1991).
H. Jones, "Splat Cooling and Metastable Phases," Rep. Prog. Phys. 36, 1425 (1973).

*Primary Examiner*—George Wyszomierski
*Attorney, Agent, or Firm*—Choate, Hall & Stewart

[57] ABSTRACT

A thermal reactor system that produces nanoscale powders by ultra-rapid thermal quench processing of high-temperature vapors through a boundary-layer converging-diverging nozzle. A gas suspension of precursor material is continuously fed to a thermal reaction chamber and vaporized under conditions that minimize superheating and favor nucleation of the resulting vapor. According to one aspect of the invention, the high temperature vapor is quenched using the principle of Joule-Thompson adiabatic expansion. Immediately after the initial nucleation stages, the vapor stream is passed through the nozzle and rapidly quenched through expansion at rates of at least 1,000° C. per second, preferably greater than 1,000,000° C. per second, to block the continued growth of the nucleated particles and produce a nanosize powder suspension of narrow particle-size distribution. According to another aspect of the invention, a gaseous boundary-layer stream is injected to form a blanket over the internal surface of the nozzle to prevent vapor condensation in the throat of the nozzle and its potential failure.

17 Claims, 16 Drawing Sheets

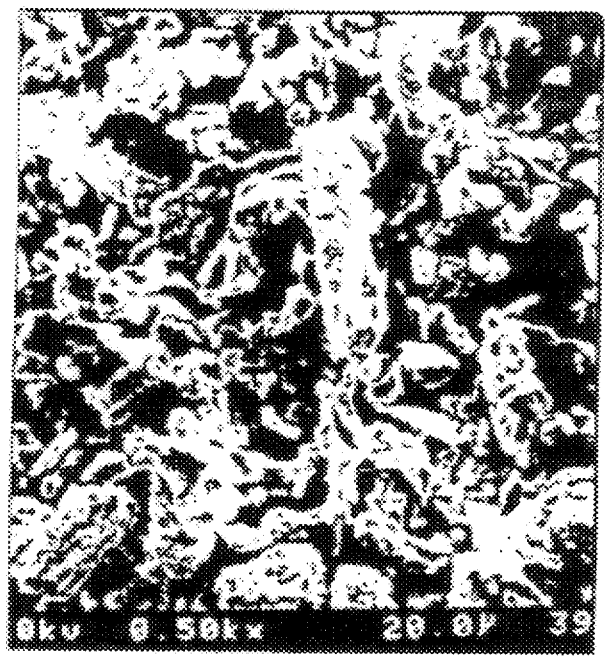
Titanium
FIG. 8
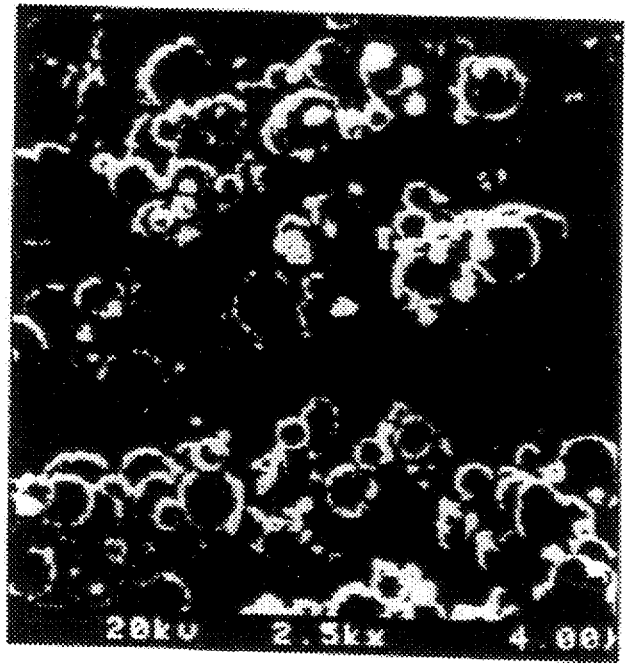
Iron

METHOD OF PRODUCING NANOSCALE POWDERS BY QUENCHING OF VAPORS

BACKGROUND OF THE INVENTION

1. Field of the Invention

This invention pertains in general to apparatus for the rapid solidification of high temperature vapors. In particular, the invention relates to a novel approach to thermal quenching based on adiabatic expansion of the vapor through a boundary layer converging-diverging nozzle.

2. Description of the Prior Art

Rapid solidification processing of high temperature liquids and vapors has been extensively researched. See Loren A. Jacobson and J. McKittrick, "Rapid Solidification Processing", Materials Sciences & Eng., R-11, 355–408 (1994). Such process techniques are used to prepare fine microstructures (micron sized), increase solid solubility of alloy elements, and prepare non-equilibrium phases, particularly in powder metallurgy. Conventional rapid solidification methods, such as oil quench, gas quench, chill casting, and centrifugal atomization, achieve typical thermal quench rates of $10^2$ to $10^5$ K/sec.

Higher quench rates are very desirable because they can enable the synthesis of powders that are submicron in domain size and, at rates greater than $10^6$ K/sec, can enable the synthesis of powders with domain size less than 100 nanometers. As defined in the art, submicron powders are materials having average grain size below 1 micrometer. Of particular interest are nanoscale powders; namely, submicron powders with grain size less than 100 nanometers. Finer domain sizes are desirable because the physiochemical properties of materials are remarkably different and commercially useful when the domain size is reduced below 100 nanometers. Nanoscale powders also exhibit very high surface areas and enhanced surface activity for physical and chemical reactions.

It is known that within these size ranges a variety of confinement effects occur that dramatically change the properties of the material. A property will be altered when the entity or mechanism responsible for that property is confined within a space smaller than some critical length associated with that entity or mechanism. Thus, for example, a normally ductile metal will become significantly harder if its grain size is reduced to the point where moving dislocations through its crystal lattice are no longer able to occur at normal levels of applied stress. Therefore, confinement effects can be exploited to produce extremely hard and strong materials with much higher yield stress than exhibited by the conventional form of their precursors. The same principle has also been used to manufacture unique optical materials with grain sizes tailored for excitonic interactions with particular wavelengths; electroceramics with unique electronic and electrical characteristics; superplastic ceramics with grain sizes engineered to allow low cost, rapid net-shape forming of ceramics as a substitute process for machining of ceramics; catalysts with extremely high surface areas, high selectivity and activity; materials with unique electrochemical properties; and materials that exhibit unprecedented magnetic properties. In view of these results, submicron powders in general, and nanoscale powders (nanopowders) in particular, represent an extraordinary opportunity for designing and developing a wide range of structural, optical, electrical, electronic, electrochemical, magnetic and chemical applications.

Although this extraordinary opportunity has been apparent for several years, large scale commercialization has remained unrealized because of the high cost and low throughput of known processes for producing nanopowders, the lack of process control over size and size distribution of the resulting material, the unpredictable composition of the constituent phases, and the lack of control over the nature of and the interactions among the interfaces created between the constituent phases. Nanopowders may indeed represent the threshold of a new era in materials technology, but the key to their full utilization depends on the development of new processes for producing nanopowders economically and in commercially viable quantities under controlled operating conditions.

In recent years, several methods have been used for producing nanopowders and the materials produced by this prior-art technology have confirmed the fact that nanopowders possess important technical properties that show the potential for becoming commercially significant. However, all known production methods consist of batch processes that are too expensive to yield commercially affordable materials for bulk applications (current production costs for these processes are orders of magnitude higher than the $10.00/lb target price considered economical for bulk applications of these materials). Therefore, the commercial future of nanopowders depends on the development of a process and apparatus that can produce nanopowders with predetermined properties, in commercially viable quantities, and at an affordable cost.

Ideally, the synthesis and processing technology for nanopowders should allow control of the size and size distribution of the constituent structures and phases (this is critical to the mechanistic performance of nanopowders); allow control of the composition of the phases in the nanomaterial (critical to define the property domain of the nanomaterial); and allow control over the nature of interfaces (e.g. purity) and the interaction between the interfaces (critical to the interface-based characteristics of the nanopowders). None of the known processes for the synthesis of nanomaterials possesses these characteristics; therefore, none is suitable for bulk commercialization of nanopowders.

In particular, prior-art processes are all batch, and have high energy or solvent processing requirements, which are all inherent limitations to the cost-effective and large-scale production of nanopowders. The processes currently in use can be classified into three general groups: chemical, mechanical-attrition, and gas-condensation methods. The chemical methods include precipitation techniques, sol-gel processes, and inverse-micelle methods. These processes have been used to successfully synthesize narrowly distributed nanopowders; however, being chemical-media based, the resulting nanopowders are covered with chemical surface layers. This surface covering adversely affects the properties of the nanopowders and inhibits their further processing into bulk materials. In addition, the use of solvents and chemicals has a significant economic impact on the synthesis process because of the cost of chemicals and the pollution remediation required by their use.

The mechanical attrition methods rely on the physical decomposition of coarser grains through severe mechanical deformation. Such processing methods are energy intensive, have low flexibility, are susceptible to contamination by attrition tools or media, and afford little control over the quality and consistency of the final product.

The gas condensation methods essentially involve the evaporation of a coarse (at least micron size) source of precursor material, such as a metal, inorganic, etc., in an inert gas at a low pressure. The evaporated source atoms or molecules collide with the gas atoms or molecules and lose energy, thereby causing a homogeneous condensation of atom or molecule clusters in the supersaturated vicinity of the precursor source. The further accretion and/or coalescence of the nucleated particles is minimized by rapid removal of the nanometer-sized powders so formed from the region of supersaturation. See R. Uyeda, "Studies of Ultrafine Particles in Japan: Crystallography, Methods of Preparation and Technological Applications," Prog. Mater. Sci., 35, 1 (1991), and R. W. Siegel, "Materials Science and Technology," 15, VCH, Weinhem, 583 (1991). Alternatively, gas condensation processes may involve gas-phase reactions. Some of the known gas condensation processes have produced nanomaterials of acceptable size, but they are all batch operations and are not readily scaleable for commercial exploitation.

Our copending application entitled "Integrated thermal process and apparatus for the continuous synthesis of nanoscale powders," filed concurrently with this disclosure, describes a process for producing nanoscale powders that utilizes quenching at rates greater than $10^6$ K/sec to produce nanopowders under controlled conditions. Such higher quench rates can lead to unique non-equilibrium structures that enhance the solubility of solute elements in the bulk matrix.

To achieve higher cooling rates, contact quenching methods such as splat cooling and glazing have been suggested. See Jones, "Splat Cooling and Metastable Phases," Rep. Progr. Phys., 36, 1425 (1973). However, these methods are not suitable for thermal quenching of high temperature vapors (greater than 1500K) because these temperatures lead to thermokinetic transformations from reactions at contact surfaces. These methods are also not useful for high temperature vapors of materials such as carbides, nitrides, refractory metals, alloys, and multiphase non-equilibrium phases because the high temperatures can irreversibly damage the contact surfaces. Furthermore, these prior-art methods are not suited for thermally quenching high-temperature, chemically-active vapors (such as those resulting from chemical reactions between feed components at high temperatures).

Therefore, there remains a need for a low-cost apparatus and process (less than $10/lb) that is suitable for large-scale production of nanosize powders under controlled operating conditions. Our copending application discloses a pioneering and unique thermal process that satisfies these requirements for the continuous production of bulk quantities of nanopowders. The present invention is directed at a Joule-Thompson nozzle that is particularly suited for ultra-rapid quenching and condensation of vaporized material.

SUMMARY OF THE INVENTION

A primary objective of this invention is a device that enables very-high quench rates of high-temperature vapors that can produce nanoscale powders.

Another goal is a device that is simple, easy to operate, and flexible with respect to operating parameters, so as to allow the production of multiple products.

Another objective is a device that prevents contamination of the quenched product from the materials of construction used for the quench equipment.

Yet another goal is a device that allows flexibility in the composition of the vapor quenched, in quench rates and quench volume.

Another objective is a device that can be operated with low operating and maintenance costs.

Still another objective is a device that can be operated continuously and that is suitable for scaling up to production rates in the order of tons per day.

Another goal is a device that is safe and environmentally benign.

Finally, another goal is an operationally stable device that requires minimal external controls.

According to the foregoing objectives, this invention consists of a thermal reactor system for the production of nanopowders by ultra-rapid thermal quench processing of high-temperature vapors through a boundary layer Joule-Thompson nozzle. A gas suspension of precursor material is continuously fed to a thermal reaction chamber and vaporized under conditions that minimize superheating and favor nucleation of the resulting vapor. According to one aspect of the invention, the high-temperature vapor is quenched using the principle of Joule-Thompson adiabatic expansion. Immediately after the initial nucleation stages, the vapor stream is passed through the nozzle and rapidly quenched through expansion at rates of at least 1,000° C. per second, preferably greater than 1,000,000° C. per second, to block the continued growth of the nucleated particles and produce a nanosize powder suspension of narrow particle-size distribution. Since the physical characteristics of the nozzle determine the extent of cooling, pressure drop and density drop, the condensation process can be advantageously controlled by utilizing a nozzle of predetermined key dimensions to fit the requirements of the material being condensed. According to another aspect of the invention, a gaseous boundary-layer stream is injected to form a blanket over the internal surface of the nozzle to prevent vapor condensation in the throat of the nozzle and its potential failure.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

BRIEF DESCRIPTION OF THE DRAWINGS

FIG. 8 is a scanning electron microscope image of the iron and titanium material used in Example 2, showing that the feed powders were greater than 1 micrometer.

DETAILED DESCRIPTION OF THE INVENTION

The heart of this invention lies in the development of a boundary-layer expansion nozzle adapted to implement the Joule-Thompson adiabatic expansion step required to quench condensing vapors at rates as high as $10^{6°}$ C./sec, or greater, under predictable conditions, in a process for producing nanozise powders of desired properties.

Figure 1:
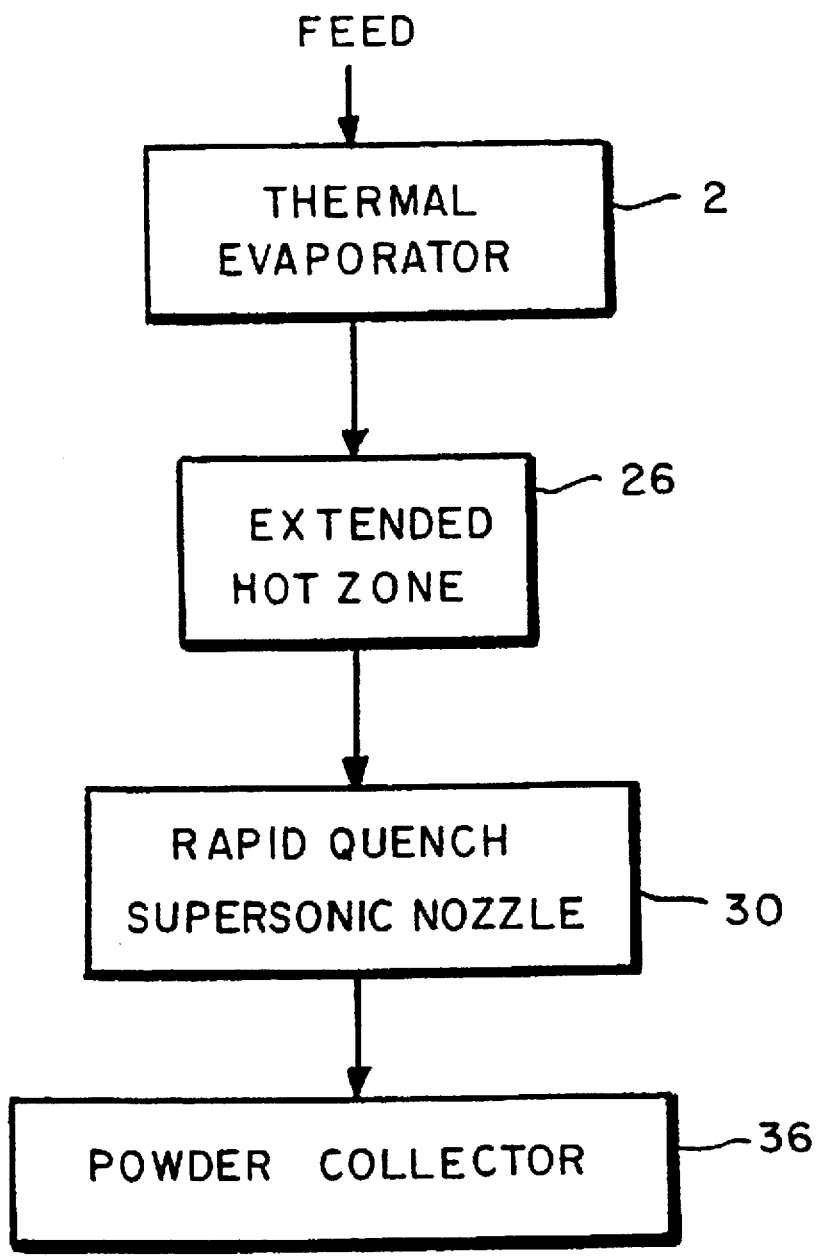
FIG. 1 is a block diagram of the thermal process of the present invention for the continuous synthesis of nanoscale powders.
Figure 2:
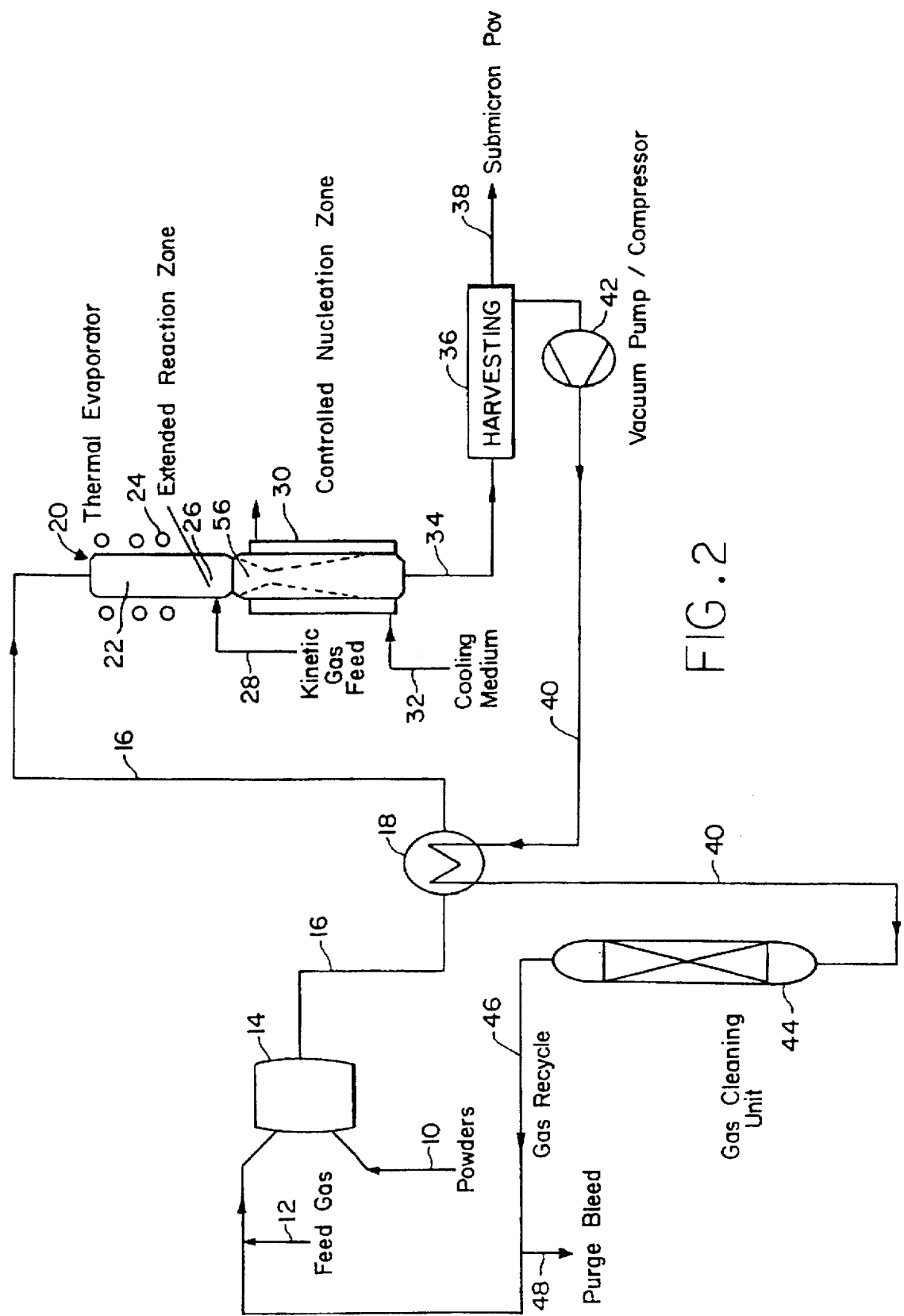
FIG. 2 is a schematic representation of the process for the continuous synthesis of nanoscale powders, including the adiabatic-expansion, thermal-quenching step of the invention.

Referring to the drawings, wherein like parts are designated throughout with like numerals and symbols, FIGS. 1 and 2 show a block diagram and a schematic flow diagram, respectively, of a thermal process for the continuous synthesis of nanoscale powders as applied to solid precursors such as metals, alloys, ceramics, composites, and combinations thereof with particle size (normally greater than 1 micrometer) suitable for continuous vaporization in a gas stream.

A feed stream 10 of a precursor material in powder form is premixed with a feed gas stream 12 (such as argon, helium, nitrogen, oxygen, hydrogen, water vapor, methane, air, or a combination thereof, depending on the particular precursor being processed and the corresponding atmosphere—inert, oxidizing, or reducing—required for the process) in mixing apparatus 14 appropriate to create a suspension. The powder 10 is suspended in the gas 12, preferably in a continuous operation, using fluidized beds, spouting beds, hoppers, or combinations thereof, as best suited to the nature of the precursor. The resulting gas-stream suspension 16 is advantageously preheated in a heat exchanger 18 and then is fed into a thermal reactor 20 where the suspended powder particles are partially or, preferably, completely evaporated in a thermal evaporation zone 22 by the input of thermal energy. The source 24 of such thermal energy may be internal energy, heat of reaction, conductive, convective, radiative, inductive, microwave, electromagnetic, direct or pulsed electric arc, nuclear, or combinations thereof, so long as sufficient to cause the rapid vaporization of the powder suspension being processed. Optionally, in order to prevent contamination of the vapor stream caused by partial sublimation or vaporization of the thermal reactor's interior walls, they may be pre-coated with the same material being processed.

The vaporized gas-stream suspension next enters an extended reaction zone 26 of the thermal reactor that provides additional residence time, as needed to complete the evaporation of the feed material and to provide additional reaction time (if necessary). As the stream leaves the reactor, it passes through a zone 56 where the thermokinetic conditions favor the nucleation of solid powders from the vaporized precursor. These conditions are determined by calculating the supersaturation ratio and critical cluster size required to initiate nucleation. Rapid quenching leads to high supersaturation which gives rise to homogeneous nucleation. The unstable vapor phase system self-nucleates on atomic clusters of critical size. Below the critical size, the clusters are unstable for a given supersaturation, while above the cluster size the free energy of the cluster is negative. For an ideal vapor phase, the radius of the critical cluster size is given by the relation $$r_n = 2\gamma V/kT\ln(P_1/P_{00}), \quad (1)$$

where $\gamma$ is the surface free energy, V is the molecular volume of the condensed phase, k is Boltzman's constant, $P_1$ is the pressure of the vapor in the system, and $P_{00}$ is the vapor pressure of the condensed phase. See G. S. Springer, *Advances in Heat Transfer*, 14, 281–341, Academic Press (1978).

Using titanium powder as an example, based on the physical properties of the feed material and operating conditions in the reactor (size=10μ, melting point=1,660° C., boiling point=3,287° C., heat of vaporization of titanium= 10.985 Btu/g, hot gas temperature=4,000° C.), it is possible to calculate the residence time required for vaporization (2.32 msec for heating to melting point, 0.265 msec for melting, 5.24 msec for vaporization; total time required= 8–10 msec). Based on the velocity of the suspension injected into the reactor and the travel distance through the reactor, one can determine that a velocity of about 46 ft/sec produces a residence time of 10.7 msec, sufficient for vaporization. If the process requires a predetermined thermokinetic state of the powder being processed which can be enhanced by the presence of a particular gas, a kinetic gas feed 28 (such as argon, helium, nitrogen, oxygen, hydrogen, water vapor, methane, air, or combinations thereof) can also be mixed with the precursor vapor to reach the desired thermokinetic state. As soon as the vapor has begun nucleation, the process stream is quenched in a converging-diverging nozzle-driven adiabatic expansion chamber 30 at rates at least exceeding $10^3$ K/sec, preferably greater than $10^6$ K/sec, or as high as possible. As further detailed below, a cooling medium 32 is utilized for the converging-diverging nozzle to prevent contamination of the product and damage to the expansion chamber 30. Rapid quenching ensures that the powder produced is homogeneous, its size is uniform and the mean powder size remains in submicron scale.

The quenched gas stream 34 is filtered in appropriate separation equipment 36 to remove the submicron powder product 38 from the gas stream. As well understood in the art, the filtration can be accomplished by single stage or multistage impingement filters, electrostatic filters, screen filters, fabric filters, cyclones, scrubbers, magnetic filters, or combinations thereof. The filtered nanopowder product 38 is then harvested from the filter 36 either in batch mode or continuously using screw conveyors or gas-phase solid transport and the product stream is conveyed to powder processing or packaging unit operations (not shown in the drawings). The filtered gas stream 40 is compressed in a vacuum-pump/compressor unit 42 and cooled by preheating the gas-stream suspension 16 in heat exchanger 18. Thus, the enthalpy of compression can be utilized by the process as process heat through heat integration. Stream 40 is then treated in a gas cleaning unit 44 to remove impurities and any undesirable process product gases (such as CO, $CO_2$, $H_2O$, HCl, $NH_3$, etc). The gas treatment can be accomplished by single stage or multistage gas-gas separation unit operations such as absorption, adsorption, extraction, condensation, membrane separation, fractional diffusion, reactive separation, fractional separation, and combinations thereof. Finally, the treated gases 46 are recycled back to be reused with the feed gas stream 12. A small split stream 48 of the compressed treated gas 46 is purged to ensure steady state operation of the continuous thermal process.

Figure 3:
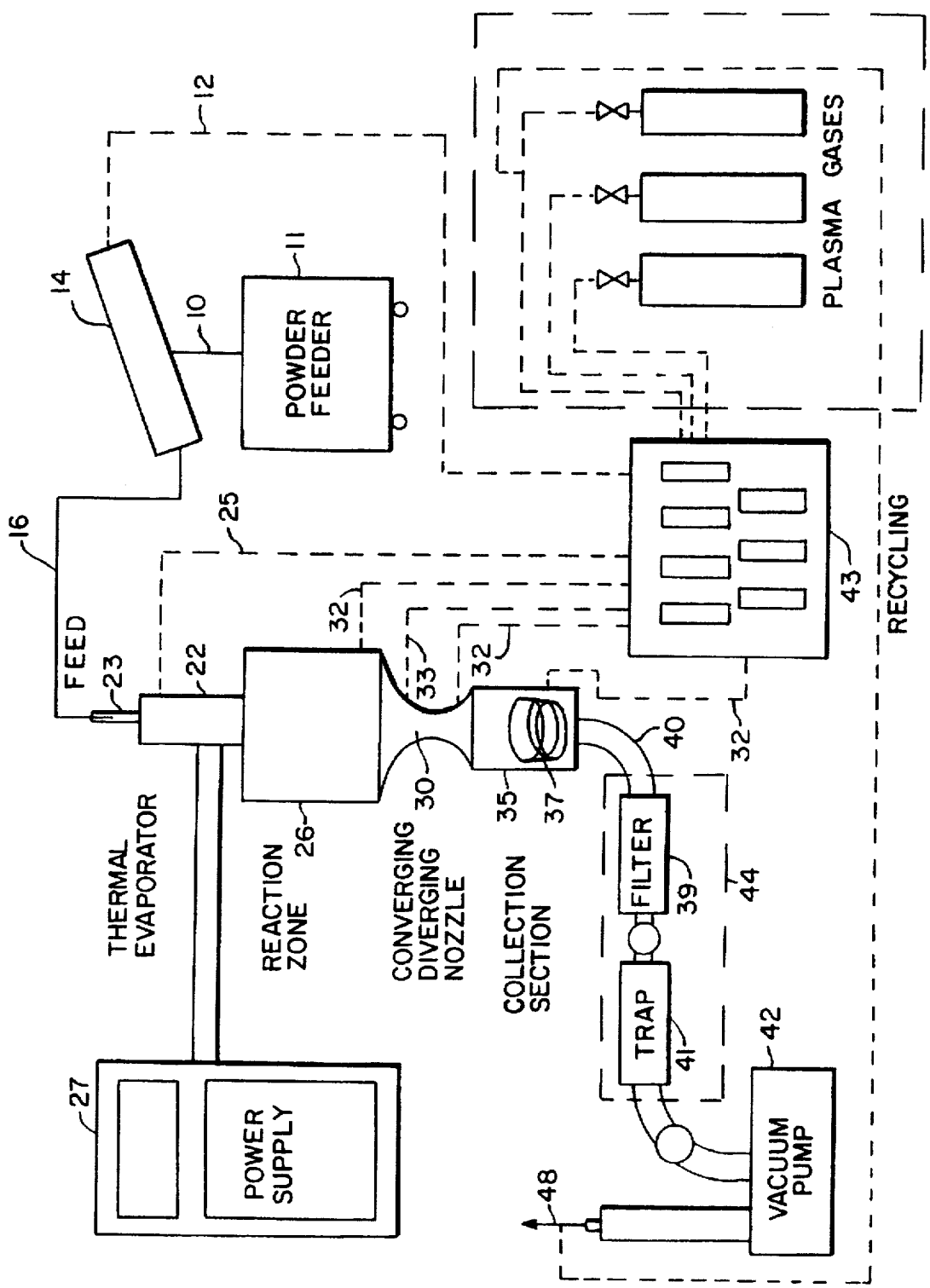
FIG. 3 is a schematic illustration of a pilot-plant process according to the preferred embodiment of the invention.

The invention was reduced to practice in a pilot plant illustrated schematically in FIG. 3. This thermal reactor system consists of an upper, cylindrical, thermal evaporation chamber 22 made of quartz and cooled by circulating water (not shown). The gas-stream suspension 16 is formed by mixing the solid feed material 10 fed by a powder feeder 11 with an inert gas stream 12, such as argon. The suspension 16 is injected continuously from the top of the thermal evaporation chamber 22 through a water-cooled injection probe 23 and is heated inductively by means of an RF plasma torch 24 (consisting of a plasma-gas source 25 and a suitable power supply 27). The reactor also comprises another, cylindrical, extended reaction zone 26 made of water-cooled stainless steel, positioned downstream of the thermal evaporation zone 22 and sufficiently large to provide the vaporized stream with the residence time required to complete the vaporization and reaction. The reaction zone 26 is lined with a zirconia refractory felt and a layer of silicon-carbide refractory material to reduce heat losses from the hot reaction zone. If necessary to prevent contamination of the reacting fluid by the reactor or refractory material, the reactor's interior walls (and refractory lining) may be further lined with the same material constituting the solid feed.

The adiabatic expansion chamber 30 consists of a Joule-Thompson converging-diverging nozzle (also known as a deLaval nozzle) having uniformly converging and diverging sections, as also illustrated in detail in FIG. 4. The nozzle is operated with a pressure drop (created by the vacuum pump 42 operated at least 50 Torr, normally between 100 and 650 Torr) sufficient for quenching the high-temperature vapors produced upstream in the reactor by plasma induction. The separation system 36 of the invention is realized by means of a collection chamber 35, attached to the outlet of the expansion chamber 30, where the very fine particles entrained in the gaseous stream are collected on a water-cooled metallic coil 37 (copper was used successfully for the test runs detailed below) and periodically extracted. It is anticipated that commercial-scale equipment would incorporate a screw or similar conveyor for the continuous removal of the nanopowder product from the collection chamber 35. The gas stream 40 out of the collection chamber is further passed through a filter 39 and trap 41 to thoroughly clean it prior to passage through the vacuum pump 42. A monitor and fluid-control panel 43 is utilized to monitor process variables (temperatures, pressures, water and gas flow rates), record them, and control all water and gas streams to maintain steady-state operation. It is noted that for simplicity the gas stream 48 exhausted from the vacuum pump 42 was not recycled in the demonstration plant of FIG. 3, but a commercial application would preferably do so for energy and material conservation.

The theoretical behavior of the Joule-Thompson adiabatic expansion process is described by the well-known equation:

$$T_2/T_1 = (P_2/P_1)^{(k-1)/k}, \quad (2)$$

where $T_1$ and $T_2$ are the temperatures before and after expansion, respectively; $P_1$ and $P_2$ are the pressures before and after expansion, respectively; and k is the ratio of specific heats at constant pressure and constant volume ($C_P/C_V$).

Applying Equation 1 to a temperature change occurring during adiabatic expansion, $\Delta T$, $$\Delta T/T_1 = (T_2 - T_1)/T_1 = (P_2/P_1)^{(k-1)/k} - 1; \quad (3)$$

or, for a steady state process, $$dT/dt = T_1 d[(P_2/P_1)^{(k-1)/k}]/dt, \quad (4)$$

which suggests that Joule-Thompson expansion can quench high-temperature vapors at a steady-state quench rate that depends on the rate at which the pressure is reduced across a given adiabatic expansion device. Thus, in a continuous, steady-state process, the quench rate can be changed by changing the rate of expansion, which provides a much-sought form of control over the nucleation process of nanopowders produced by vapor condensation. Since it is known that the size, size distribution and other properties of vapor condensation products depend on the speed at which the nucleating material is quenched, the adiabatic expansion approach of the present invention provides an invaluable tool, missing in all prior-art processes, for controlling the quality of the resulting nanopowders. In addition, because the process can be carried out stably in continuous fashion, it provides a suitable vehicle for large scale applications and commercial production of bulk nanomaterials.

Figure 5A:
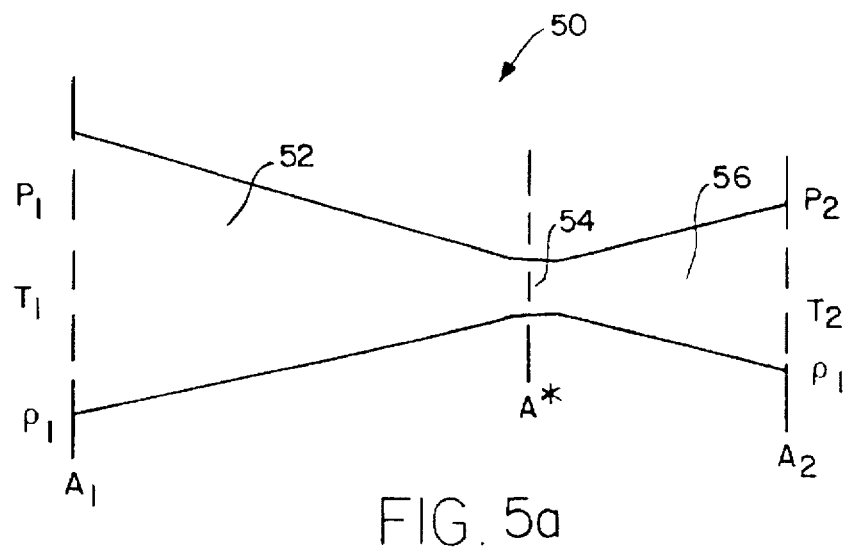
FIG. 5a is a sketch of a converging-diverging nozzle to illustrate the relationship between critical parameters of the process carried out with the nozzle of the invention.

FIG. 5a is a sketch of a converging-diverging nozzle 50 to illustrate the relationship between critical parameters of the process and of the nozzle used to carry out the invention. It consists of an optimally-shaped combination of a convergent section 52, a throat section 54, and a divergent section 56. At steady state, the condensing fluid is restricted through a uniformly decreasing cross-section $A_1$ from an initial cross-section $A_1$ at pressure $P_1$ and temperature $T_1$, it is passed through the cross-section $A^*$ of the throat 54, and then it is expanded through a final cross-section $A_2$ at pressure $P_2$ and temperature $T_2$. The process is carried out through a cross-section A that is first uniformly decreasing and then uniformly increasing through the device. In the converging section 52, the Mach number M for the nozzle is less than 1, while it is equal to 1 in the throat 54, and greater than 1 in the diverging section 56. (Mach number is defined as the ratio of the hydrodynamic flow velocity to the local speed of sound.) Therefore, the initial subsonic flow is accelerated in the converging section of the nozzle, and the flow expands supersonically in the divergent section of the nozzle. At any cross-section A, the Mach number is given by the local value of A/A*, with m=1 at the throat. Provided the flow is accelerated to a uniform design Mach number, the extent of cooling, pressure, and density drop can be predicted by the following one-dimensional relationships:

$$T_2/T_1 = [1+(k-1)M^2/2]^{-1} \quad (5)$$

$$P_2/P_1[1+(k-1)M^2/2]^{k/(k-1)} \quad (6)$$

$$\rho_2/\rho_1 = [1+(k-1)M^2/2]^{1/(k-1)} \quad (7)$$

where $T_2$, $P_2$ and $\rho_2$ are the flow temperature, pressure and density of the condensing fluid after the divergent section, $T_1$, $P_1$ and $\rho_1$ are at the inlet section of the nozzle, M is the Mach number, and K is the ratio of heat capacities at constant pressure and constant volume ($C_p/C_v$). See J. D. Anderson, *Modern Compressible Flow*, McGraw-Hill, N.Y., N.Y., (1990).

Figure 5B:
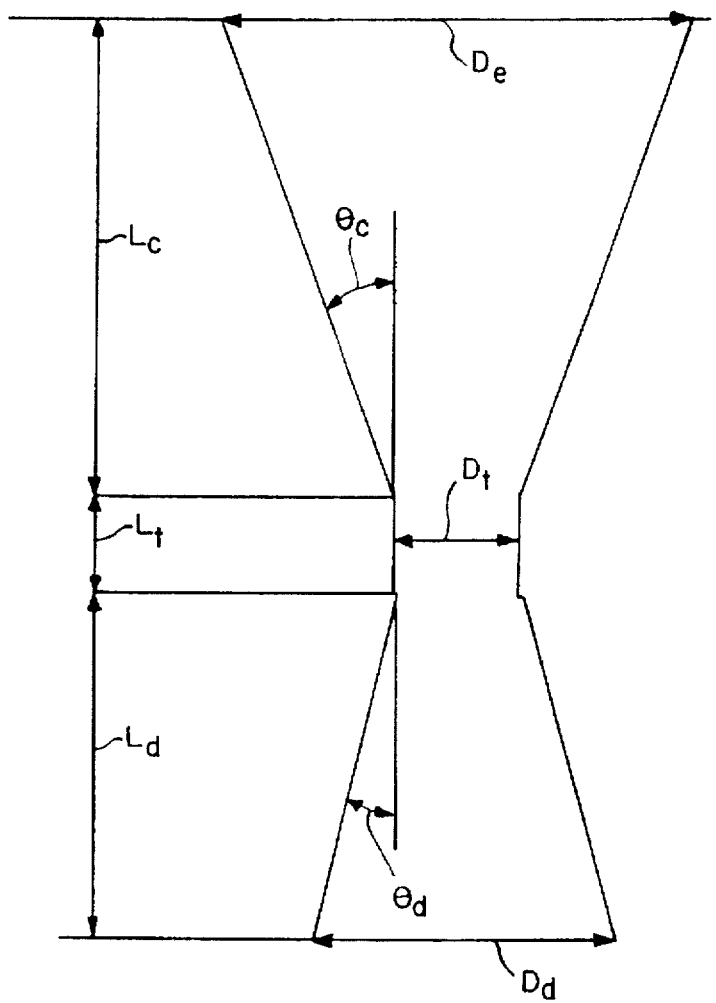
FIG. 5b is a simplified drawing of the expansion nozzle of the invention to illustrate the key design parameters for the process.

Based on these equations, it is clear that the dimensions of the nozzle are key to its performance as a quenching device. In particular, by the selection of diameter and length of the three critical sections (52, 54 and 56) and the convergent and divergent angles of the corresponding sections, it is possible to design a nozzle that will produce the necessary Mach number to yield the desired quenching rate. A simple drawing of such a converging-diverging nozzle is also shown in FIG. 5b to illustrate the key design parameters of the device. They are the diameter $D_c$, the length $L_c$ and the converging angle $\Theta_c$ for the converging section; the diameter $D_d$, the length $L_d$ and the diverging angle $\Theta_d$ for the diverging section; and the diameter $D_t$ and length $L_t$ for the throat. In the preferred embodiment of the invention, the dimensions used on the basis of the previously stated equations were as follows: $D_c$=3.0 in, $L_c$=4.125 in, $\Theta_c$= 17.965°, $D_d$=0.75 in, $L_d$=1.261 in, $\phi_d$=9.648°, $D_t$=0.325 in, and $L_t$=0.114 in.

For example, using argon as the medium, with a pressure drop of 0.72 atmospheres across the nozzle, a temperature drop of $T_2/T_1$=0.54 can be expected across the nozzle. It should be noted that in the preferred nozzle, as further detailed below, besides the cooling effect due to expansion, the temperature drop across the nozzle is also enhanced by heat transfer with a boundary-layer gas blanket in the nozzle and by water cooling of the nozzle itself.

Referring back to FIGS. 4a and 4b, the particulars of the nozzle 50 of the invention, as adapted to a process for rapidly quenching condensing vapors to produce nanopowders, are illustrated in sectional-elevational and top views. For durability and continuous operation, it is necessary to keep the nozzle wall cool to avoid contamination of the quenched product with the material of construction of the nozzle or, in worst cases, even to avoid melt down and structural failure of the nozzle. Keeping the nozzle wall cool enhances the quenching effect of the nozzle, leading to yet higher quench rates (exceeding $10^6$ K/sec). Accordingly, the temperature of the nozzle is maintained low with a coolant stream 32, such as cooling water, circulating in a cooling jacket 29 surrounding the nozzle's interior wall 58 between inlet and outlet ports 60 and 62. The cooling medium is preferably circulated in countercurrent flow to optimize uniform cooling of the wall.

Figure 4A:
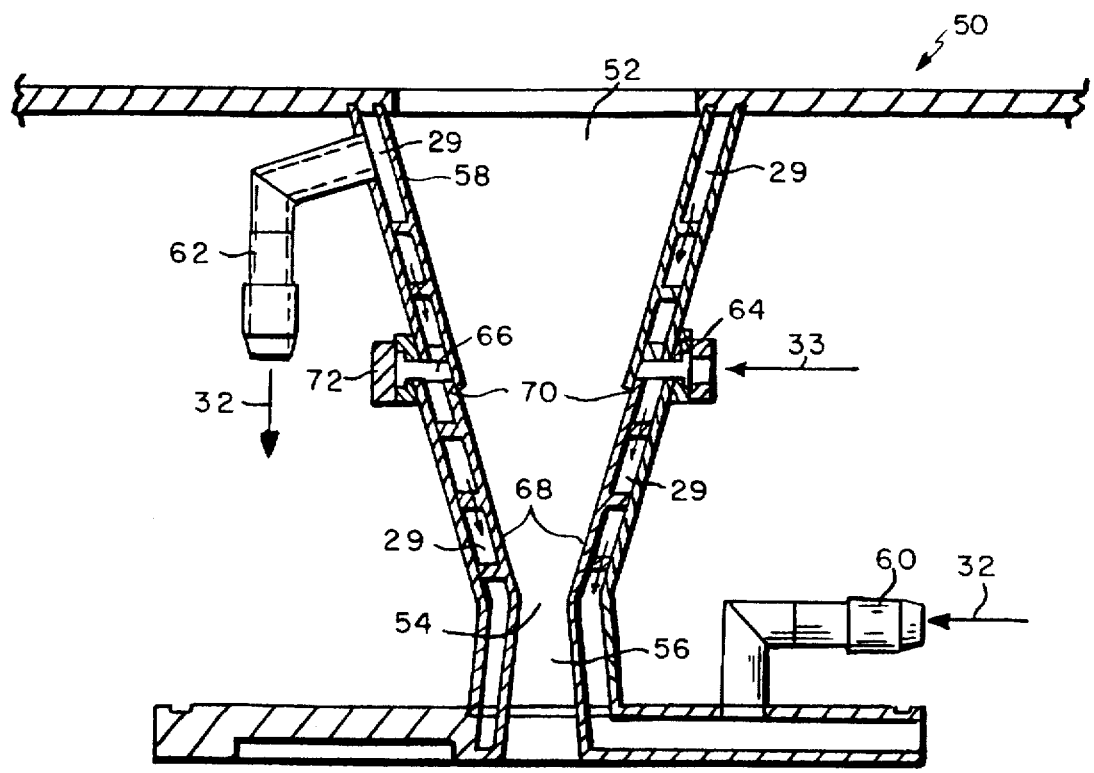
FIGS. 4a and 4b are cross-sectional elevational and top drawings, respectively, of a converging-diverging, adiabatic expansion nozzle according to the preferred embodiment of the invention.
Figure 4B:
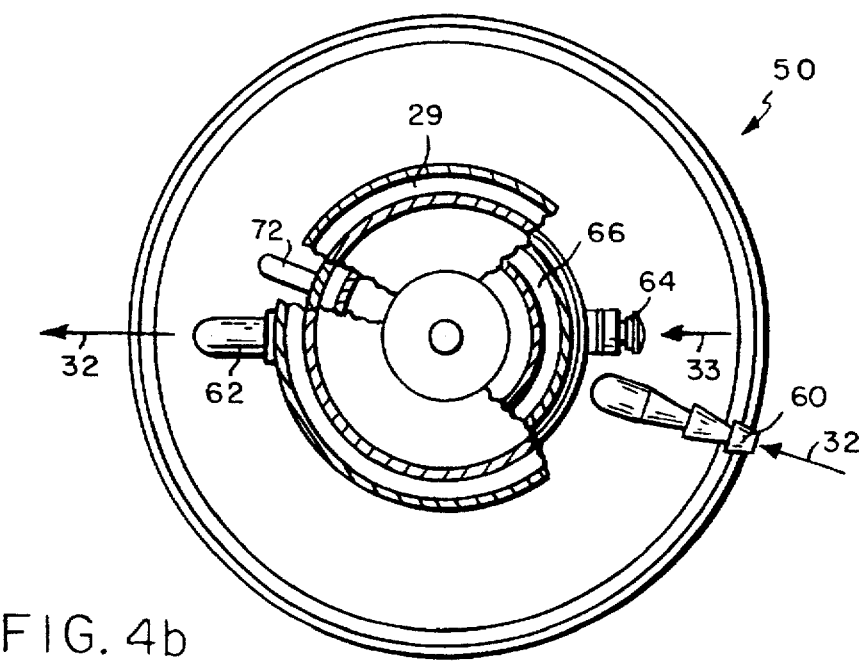

In addition, although lower nozzle-wall temperatures improve the contamination and failure problems, such lower temperatures can also lead to vapor condensation on the nozzle walls because of mechanisms such as thermophoresis. Vapor condensation can, in turn, lead to increasing restriction in the nozzle throat diameter, with subsequent closure of the throat and failure of the nozzle. We solved this additional problem by providing a gaseous boundary-layer stream 33 to form a gas blanket over the internal surface of the nozzle. In the embodiment of FIGS. 4a and 4b, the stream 33 is injected into the nozzle 50 through an inlet port 64 approximately halfway along the interior wall 58 of the converging section 52. The gaseous stream 33 is contained in an annular cavity 66 from where it is released downward, along the lower portion 68 of wall 58, through an annular slit 70 adapted to inject the gas in blanket form at the boundary with the wall. A bypass duct 72 is utilized in the embodiment of FIG. 4 to connect the upper and lower portions of the coolant jacket 29 separated by the gas cavity 66. The blanket gases can be introduced equivalently into the nozzle's interior wall axially, radially or tangentially, through the inlet port 64 and corresponding slits 70, and can be inert, such as argon or helium when metals and alloys are being processed; or reactive, such as nitrogen when nitrides are being synthesized, oxygen or air when oxides are being processed, methane and hydrocarbons when carbides are being processed, halogens when halides are being synthesized, or combinations thereof, depending on the ultimate material being synthesized. Thus, reactive gases can participate in heat transfer with the nucleation process, or reactively on powder surface to selectively modify the composition of the surface (coated powders), or reactively to transform the bulk composition of the powder, or in combinations thereof. This secondary gas feed 33 can also be helpful in engineering the product nucleation process and the resultant characteristics of the powder.

The effectiveness of the invention was demonstrated by utilizing the system of FIG. 3, which included a nozzle as shown in FIG. 4, to produce submicron powders of several different materials. In each case, the powders harvested were characterized for phases, size, morphology, and size distribution. X-ray diffraction (XRD) was used to determine the phases present in the samples using a Siemens D5000 difractometer with Ni-filtered Cu Kα radiation. The peak widths for average grain size analysis were determined by a least-square fit of a Cauchy function. The average size of the powder produced was stimated by Scherrer's method. Transmission electron microscopy (Hitachi TEM H-8100 equipped with a Kevex® EDX) was used for size, morphology, and size distribution. The particle size of the powders produced was in the nanometer range. Scanning electron microscopy (SEM) was used for the coarser size feed powders.

EXAMPLE 1

Figure 6:
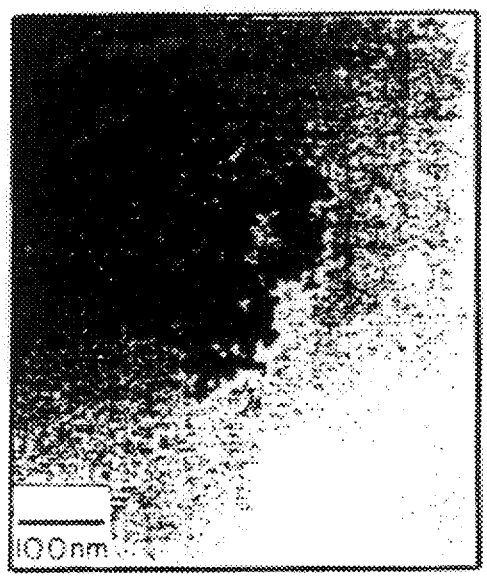
FIG. 6 is a transmission electron microscope image of the zinc nanopowder produced in Example 1.
Figure 7:
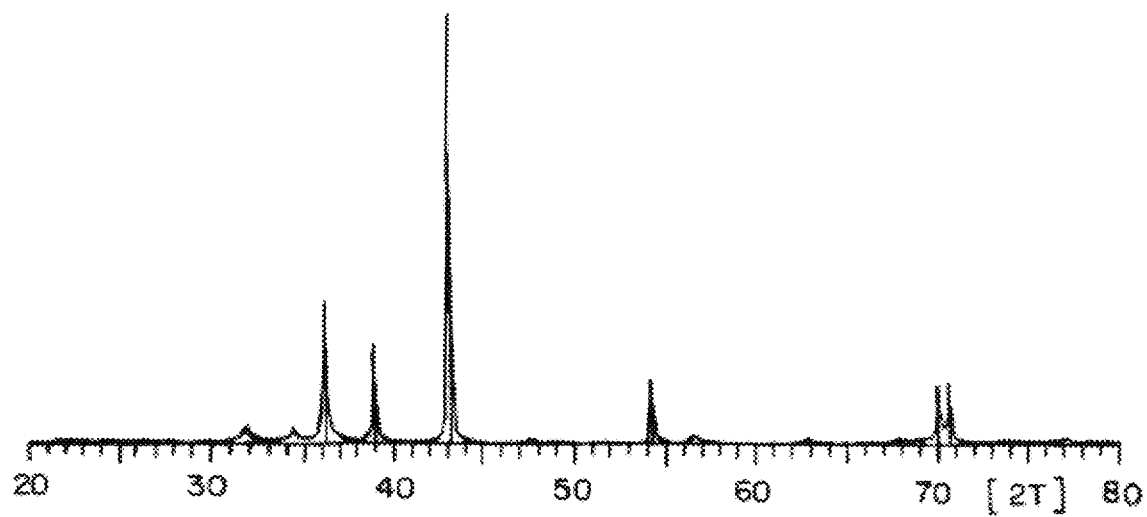
FIG. 7 is an X-ray diffraction pattern of the product of Example 1, indicating that the phase formed was zinc.

Zinc: Commercially available zinc powder (−325 mesh) was used as the precursor to produce nanosize zinc powder. Feed zinc powder was fed into the thermal reactor suspended in an argon stream (argon was used as the plasma gas; the total argon flow rate was 2.5 ft³/min). The reactor was inductively heated with 16 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. FIG. 6 is the TEM micrograph (or nanograph) of the nanosize powder produced by the invention, showing it to be in the 5–25 nanometer range. The size distribution was narrow, with a mean size of approximately 15 nm and a standard deviation of about 7.5 nm. Variations in the operating variables (such as power input, gas pressure, gas flow rates, and nozzle throat size) affected the size of the powder produced. An XRD pattern of the product is shown in FIG. 7, which indicates that the only phase present was zinc. To avoid condensation at the wall, argon was introduced tangentially (radial or axial injections have also been proven to be effective) at the nozzle walls. The inert gas provided cooling as well as a boundary layer to act as a barrier for any condensation on the nozzle walls.

EXAMPLE 2

Figure 9:
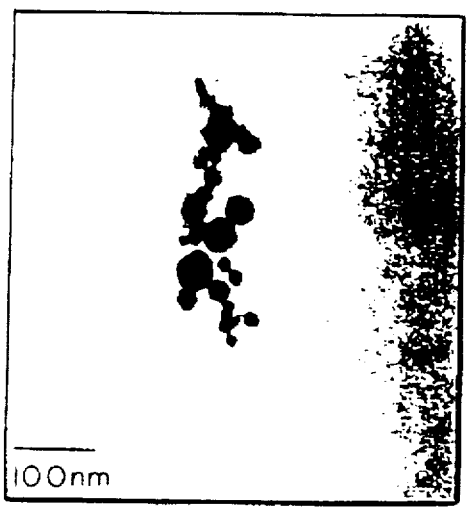
FIG. 9 is a transmission electron microscope image of the iron-titanium alloy nanopowders produced in Example 2, showing them to be in the 10–45 nanometer range.
Figure 10:
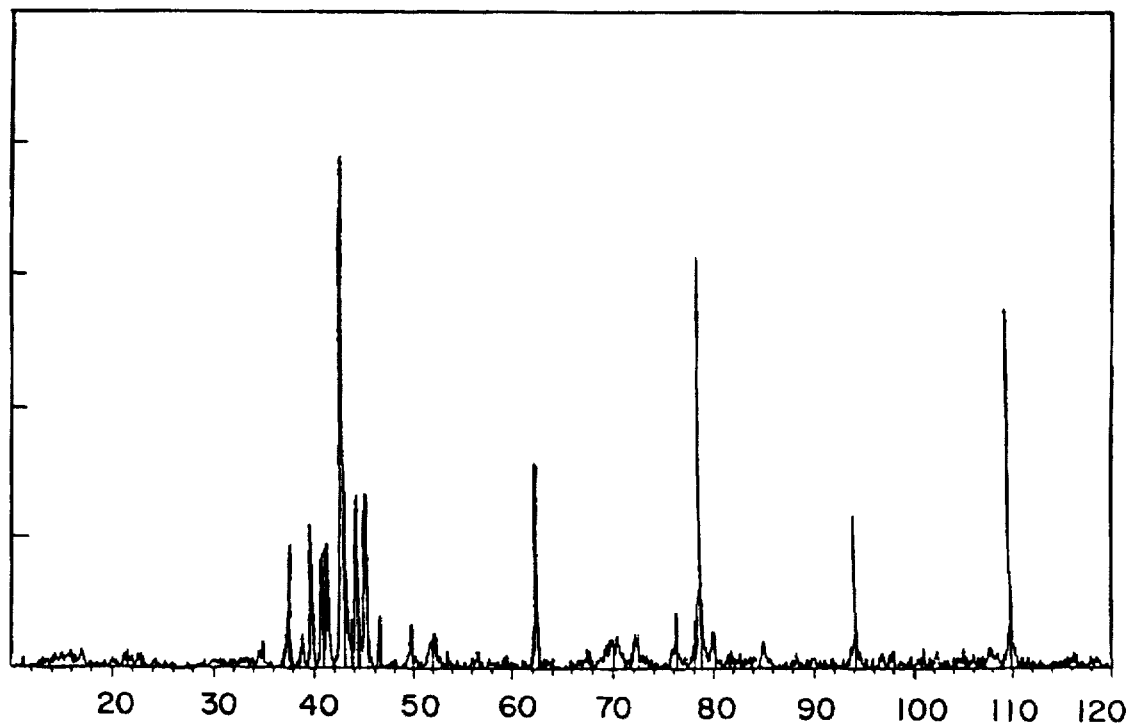
FIG. 10 is an X-ray diffraction pattern of the product of Example 2, indicating that the phases formed were titanium, iron and iron-titanium (FeTi).

Iron-Titanium Intermetallic: 2–5 micron powders of iron and 10–25 micron powders of titanium were mixed in 1:1 molar ratio and fed into the thermal reactor suspended in an argon stream (total gas flow rate, including plasma gas, was 2.75 ft$^3$/min). The reactor was inductively heated with 18 kW of RF plasma to over 5,000K in the plasma zone and above 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. FIG. 8 is the SEM micrograph of the feed powders used, showing that they were greater than 1 micrometer when fed. FIG. 9 is a TEM image of nanopowders produced by the invention, showing them to be in the 10–45 nanometer range. The size distribution was narrow, with a mean size of approximately 32 nm and a standard deviation of about 13.3 nm. Variations in the operating variables affected the size of the powder produced. The XRD pattern of the product is shown in FIG. 10, which indicates that the phases formed were titanium, iron and iron-titanium intermetallic (FeTi). The phases present illustrate that the invention can produce nanoscale powders of metals and intermetallics. To avoid condensation at the wall, argon was introduced tangentially (radial or axial injections have also been proven to be effective) at the nozzle walls. The inert gas provided cooling as well as a boundary layer to act as a barrier for any condensation on the nozzle walls.

EXAMPLE 3

Figure 11:
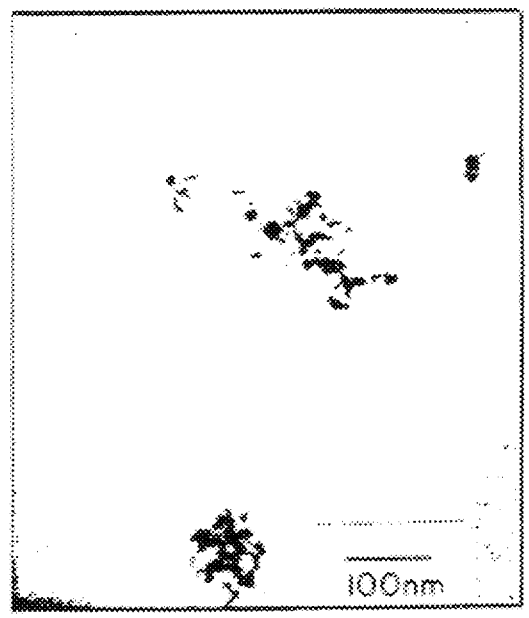
FIG. 11 is a transmission electron microscope image of the nickel aluminide nanopowder produced in Example 3.
Figure 12:
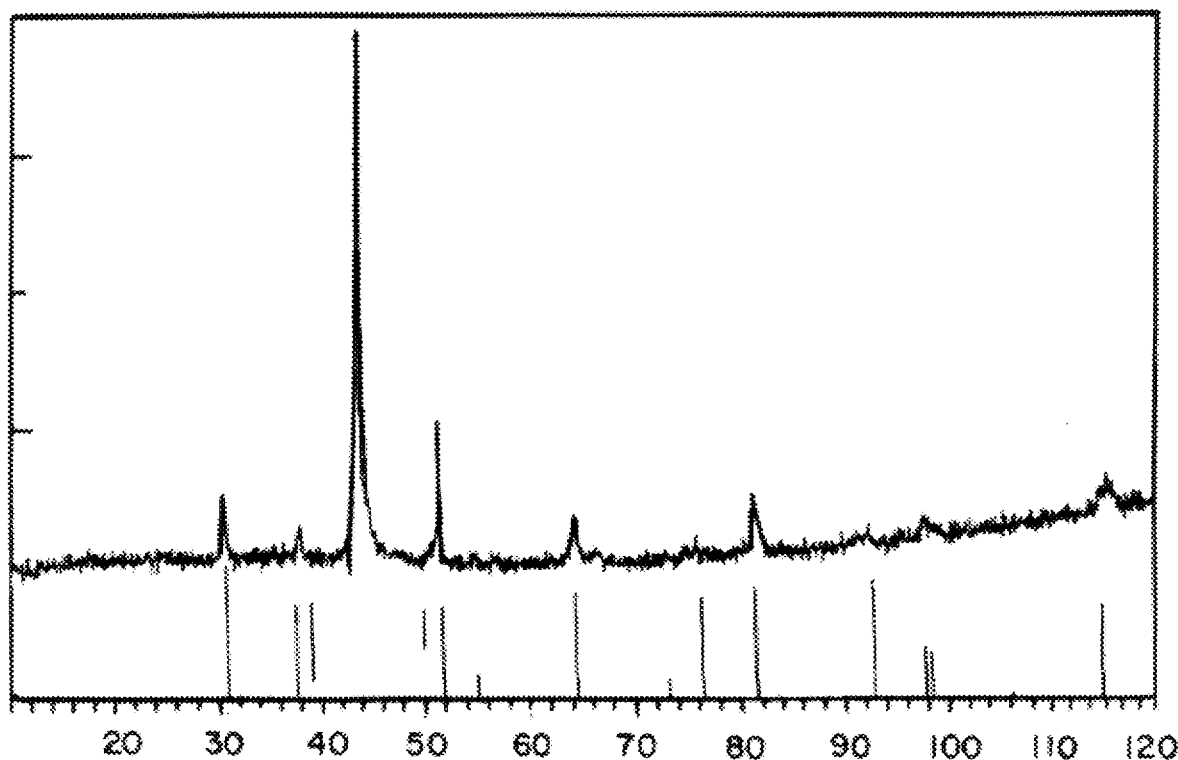
FIG. 12 is an X-ray diffraction pattern of the product of Example 3, indicating that the phase formed was NiAl.

Nickel-Aluminum Intermetallic: 1–4 micron powders of nickel and 10–30 micron powders of aluminum were mixed in 1:1 molar ratio and fed into the thermal reactor suspended in an argon stream (total feed, including plasma gas, at 2.75 ft$^3$/min). The reactor was inductively heated with 18 kW of RF plasma to over 5,000K in the plasma zone and above 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 11 is a TEM image of the nanopowder produced by the invention, showing it to be in the 10–30 nanometer range. The size distribution was narrow, with a mean size of approximately 16.4 nm and a standard deviation of about 5.2 nm. Variations in the operating variables affected the size of the powder produced. The XRD pattern of the product is shown in FIG. 12, which indicates that the phase formed was NiAl. The phases present illustrate that the invention can produce nanoscale powders of metals and intermetallics. To avoid condensation at the wall, argon was introduced tangentially at the nozzle walls. The inert gas provided cooling as well as a boundary layer to act as a barrier for any condensation on the nozzle walls.

EXAMPLE 4

Figure 13:
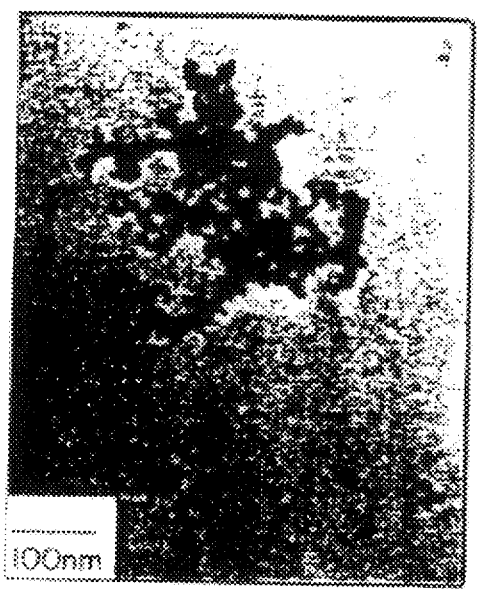
FIG. 13 is a transmission electron microscope image of the tungsten oxide nanopowder produced in Example 4.
Figure 14:
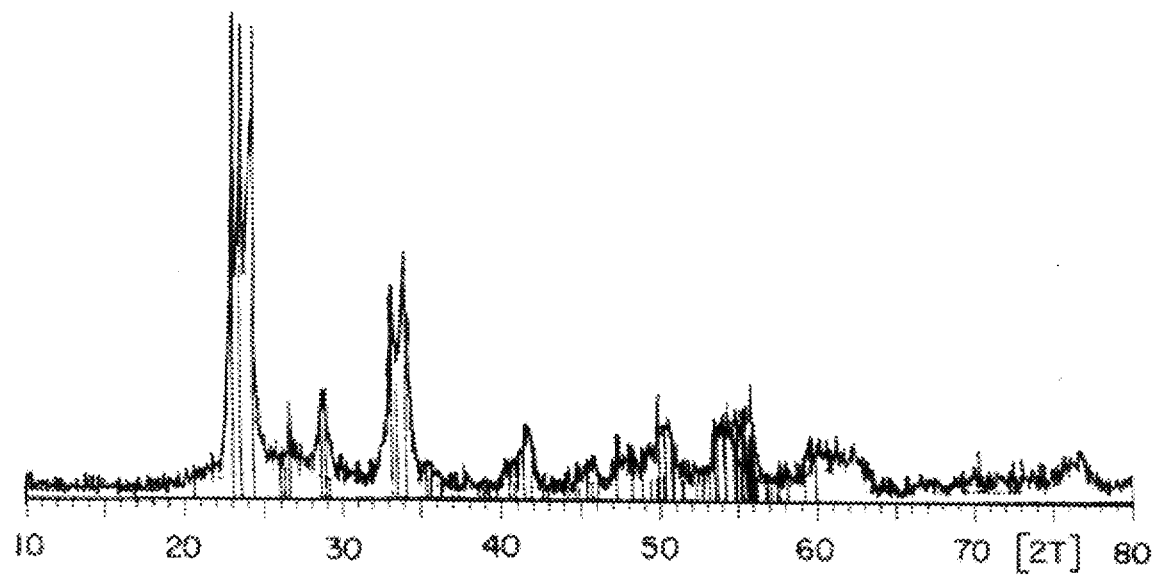
FIG. 14 is an X-ray diffraction pattern of the product of Example 4, indicating that the phase formed was $WO_3$.

Tungsten Oxide: Commercially available tungsten oxide powder (–325 mesh size) was used as the precursor to produce nanosize WO$_3$. The tungsten oxide powder was suspended in a mixture of argon and oxygen as the feed stream (flow rates were 2.25 ft$^3$/min for argon and 0.25 ft$^3$/min for oxygen). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. FIG. 13 is the TEM nanograph of the WO$_3$ powder produced by the invention, showing it to be in the 10–25 nanometer range. The size distribution was narrow, with a mean size of about 16.1 nm and a standard deviation of about 6.3 nm. Variations in the operating variables (such as power input, gas pressure, gas flow rates, and nozzle throat size) affected the size of the powder produced. An XRD pattern of the product is shown in FIG. 14, which indicates that the phase present was WO$_3$. To avoid condensation at the wall, argon was introduced tangentially at the nozzle walls. The inert gas provided cooling as well as a boundary layer to act as a barrier for any condensation on the nozzle walls.

EXAMPLE 5

Figure 15:
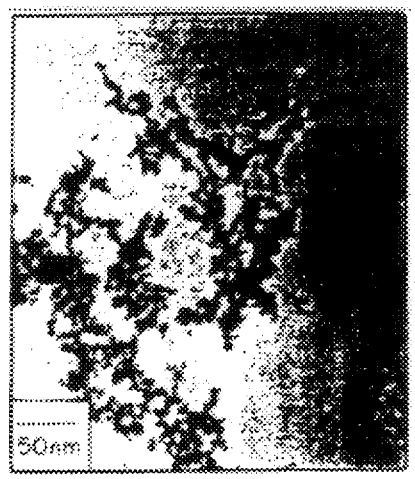
FIG. 15 is a transmission electron microscope image of the cerium oxide nanopowder produced in Example 5.

Cerium Oxide: Commercially available cerium oxide powder (5–10 micron size) was used as the precursor to produce nanosize CeO$_2$. The cerium oxide powder was suspended in a mixture of argon and oxygen as the feed stream (at total rates of 2.25 ft$^3$/min for argon and 0.25 ft$^3$/min for oxygen). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 650 Torr. The powder produced was separated from the gas by means of a cooled copper-coil-based impact filter followed by a screen filter. FIG. 15 is the TEM nanograph of the $CeO_2$ powder produced by the invention, showing it to be in the 5–25 nanometer range. The size distribution was narrow, with a mean size of about 18.6 nm and a standard deviation of about 5.8 nm.

Figure 16:
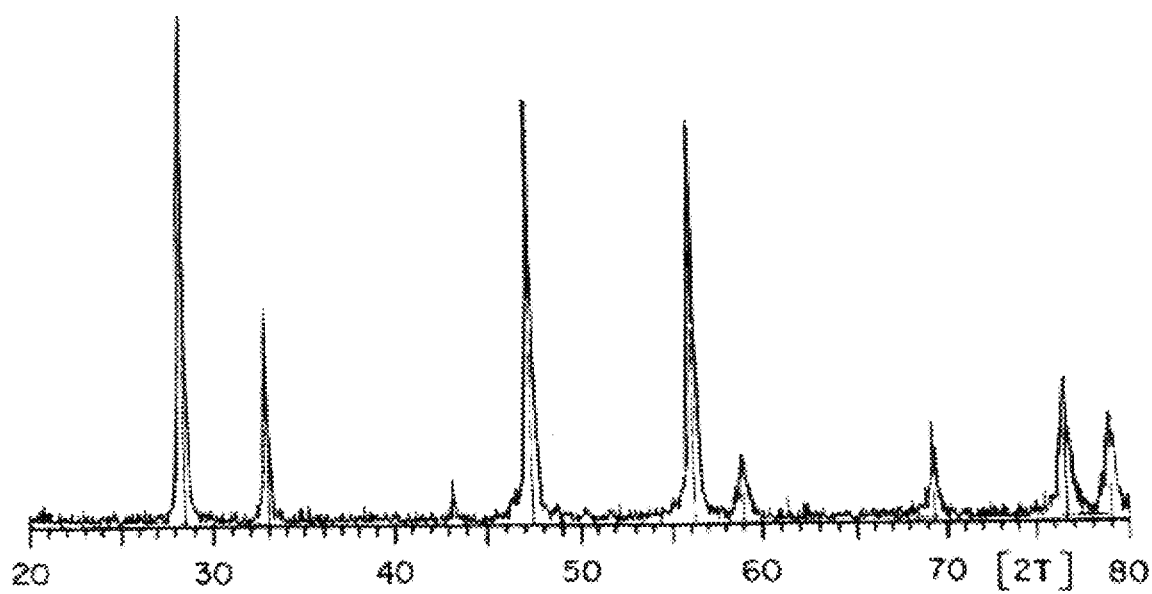
FIG. 16 is an X-ray diffraction pattern of the product of Example 5, indicating that the phase formed was $CeO_2$.

Variations in the operating variables affected the size of the powder produced. An XRD pattern of the product is shown in FIG. 16, which indicates that the phase present was $CeO_2$. To avoid condensation at the wall, argon was introduced tangentially at the nozzle walls. The inert gas provided cooling as well as a boundary layer to act as a barrier for any condensation on the nozzle walls.

EXAMPLE 6

Figure 17:
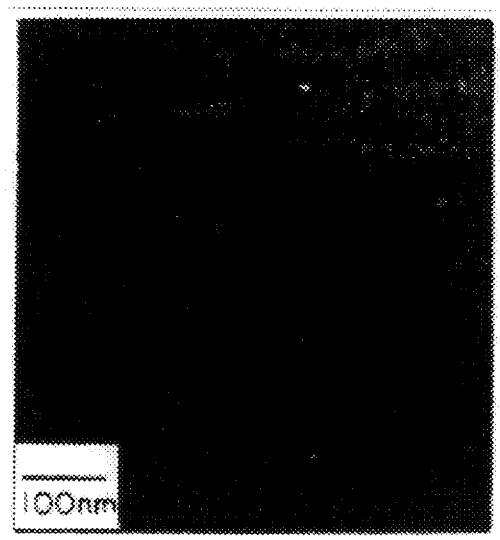
FIG. 17 is a transmission electron microscope image of the silicon carbide nanopowder produced in Example 6.
Figure 18:
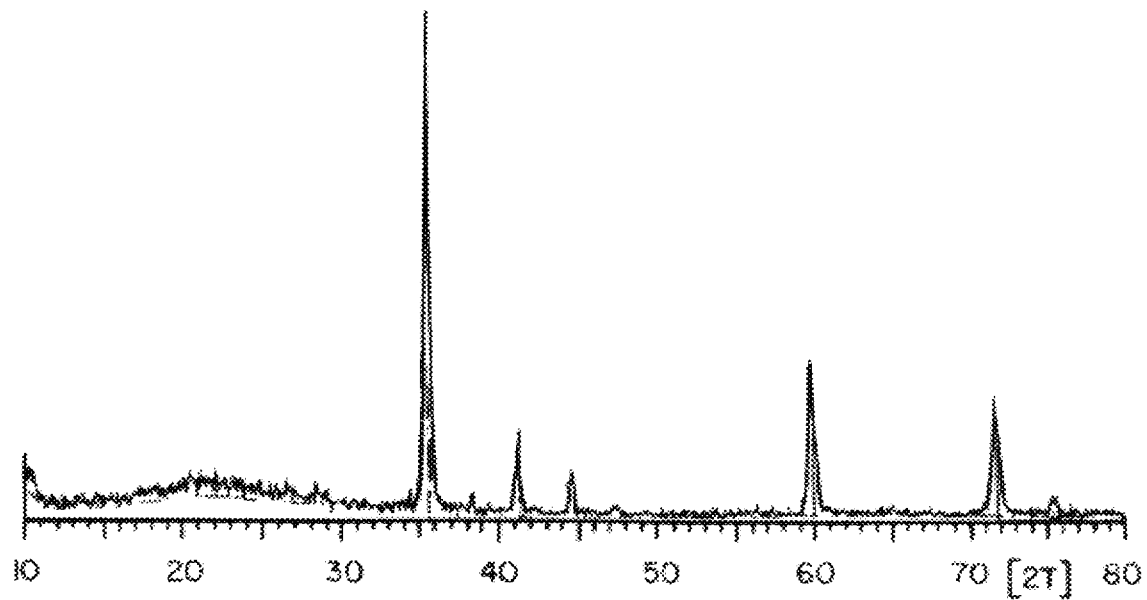
FIG. 18 is an X-ray diffraction pattern of the product of Example 6, indicating that the phase formed was SiC.

Silicon Carbide: Commercially available silicon carbide powder (−325 mesh size) was used as the precursor to produce nanosize SiC. The powder was suspended in argon as the feed stream (total argon flow rate of 2.5 ft³/min). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 17 is the TEM nanograph of the SiC powder produced by the invention, showing it to be in the 10–40 nanometer range. The size distribution was narrow, with a mean size of approximately 28 nm and a standard deviation of about 8.4 nm. Variations in the operating variables affected the size of the powder produced. An XRD pattern of the product is shown in FIG. 18, which indicates that the phase present was SiC. To avoid condensation at the wall, argon was introduced tangentially at the nozzle walls. The inert gas provided cooling as well as a boundary layer to act as a barrier for any condensation on the nozzle walls.

EXAMPLE 7

Molybdenum Nitride: Commercially available molybdenum oxide ($MoO_3$) powder (−325 mesh size) was used as the precursor to produce nanosize $MO_2N$. Argon was used as the plasma gas at a feed rate of 2.5 ft³/min. A mixture of ammonia and hydrogen was used as the reactant gases ($NH_3$ at 0.1 ft³/min; $H_2$ at 0.1 ft³/min). The reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter.

Figure 19:
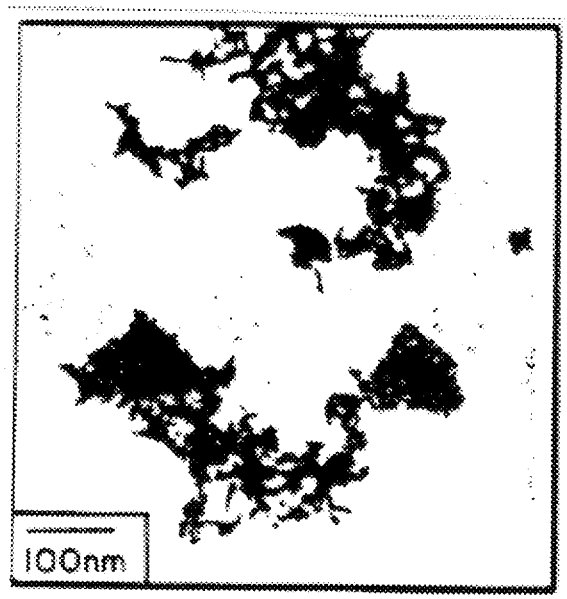
FIG. 19 is a transmission electron microscope image of the molybdenum nitride nanopowder produced in Example 7.
Figure 20:
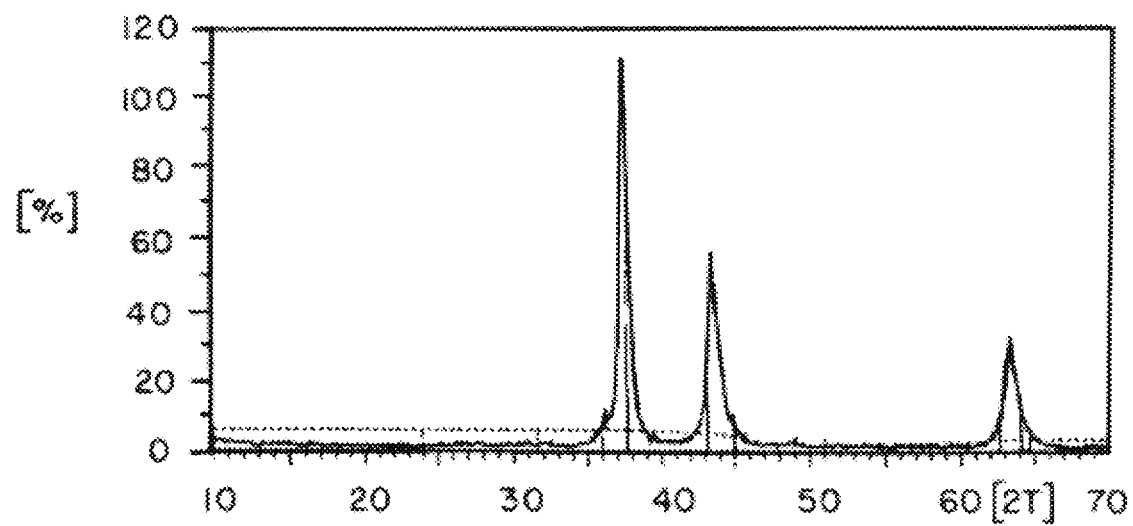
FIG. 20 is an X-ray diffraction pattern of the product of Example 7, indicating that the phase formed was $MO_2N$.

FIG. 19 is the TEM nanograph of the $Mo_2N$ powder produced by the invention, showing it to be in the 5–30 nanometer range. The size distribution was narrow, with a mean size of about 14 nm and a standard deviation of about 4.6 nm. Variations in the operating variables affected the size of the powder produced. An XRD pattern of the product is shown in FIG. 20, which indicates that the phase present was $MO_2N$. To avoid condensation at the wall, argon was introduced tangentially at the nozzle walls. The inert gas provided cooling as well as a boundary layer to act as a barrier for any condensation on the nozzle walls.

EXAMPLE 8

Figure 21:
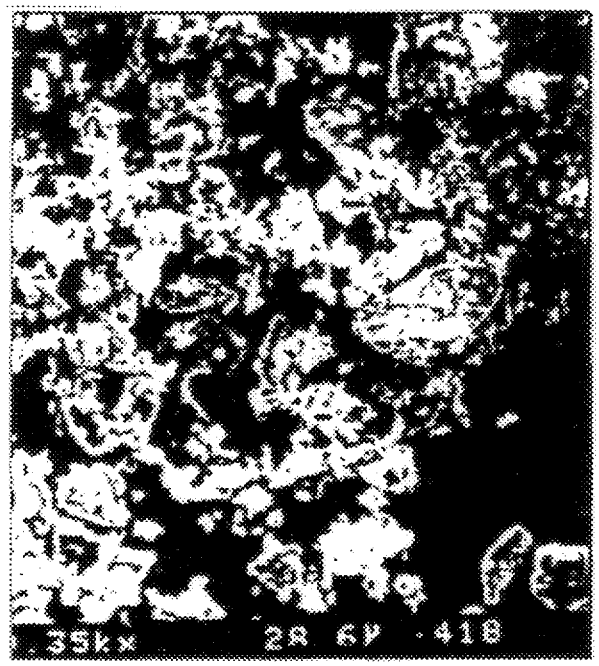
FIG. 21 is a scanning electron microscope image of the nickel boride ceramic used in Example 8, showing that the feed powder was greater than 1 micrometer.
Figure 22:
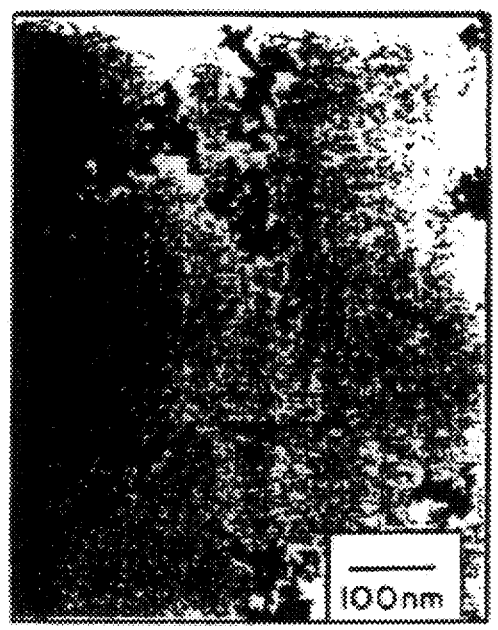
FIG. 22 is a transmission electron microscope image of the Ni and $Ni_3B$ nanopowders produced in Example 8, showing them to be in the 10–30 nanometer range.
Figure 23:
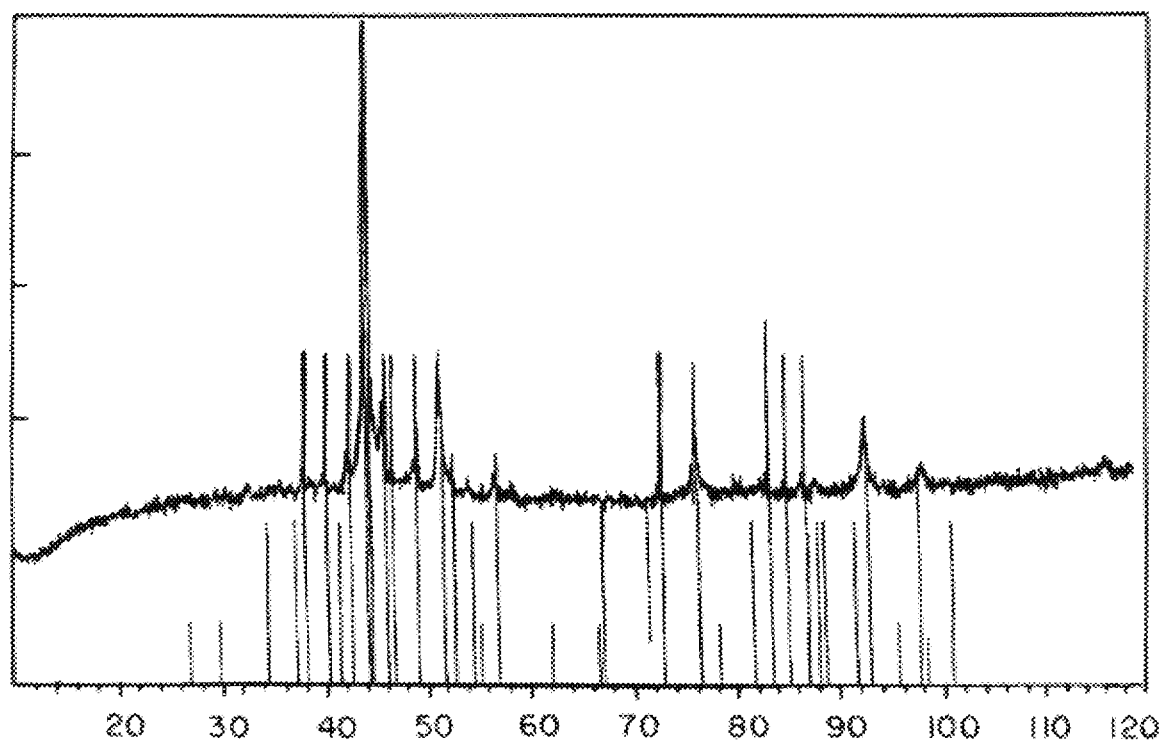
FIG. 23 is an X-ray diffraction pattern of the product of Example 8, indicating that the phases formed were Ni and $Ni_3B$.

Nickel Boride Ceramic: 10–50 micron powder of nickel boride were fed into the thermal reactor with argon (fed at a total rate, including plasma gas, of 2.75 ft³/min). Once again, the reactor was inductively heated with 18 kW of RF plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. FIG. 21 shows the SEM micrograph of the feed powders used, demonstrating that they were greater than 1 micrometer when fed. FIG. 22 is the TEM nanograph of the $Ni_3B$ powder produced by the invention, showing it to be in the 10 to 30 nanometer range. The size distribution was narrow, with a mean size of about 12.8 nm and a standard deviation of about 4.2 nm. Variations in the operating variables affected the size of the powder produced. An XRD pattern of the product is shown in FIG. 23, which indicates that the phase present were Ni and $Ni_3B$. To avoid condensation at the wall, argon was introduced tangentially at the nozzle walls. The inert gas provided cooling as well as a boundary layer to act as a barrier for any condensation on the nozzle walls.

EXAMPLE 9

Figure 24:
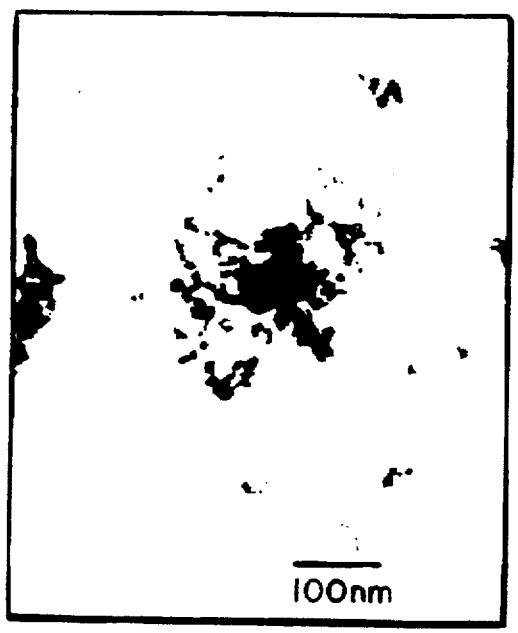
FIG. 24 is a transmission electron microscope image of the calcium-oxide nanopowders produced in Example 9, showing them to be in the 5–20 nanometer range.
Figure 25:
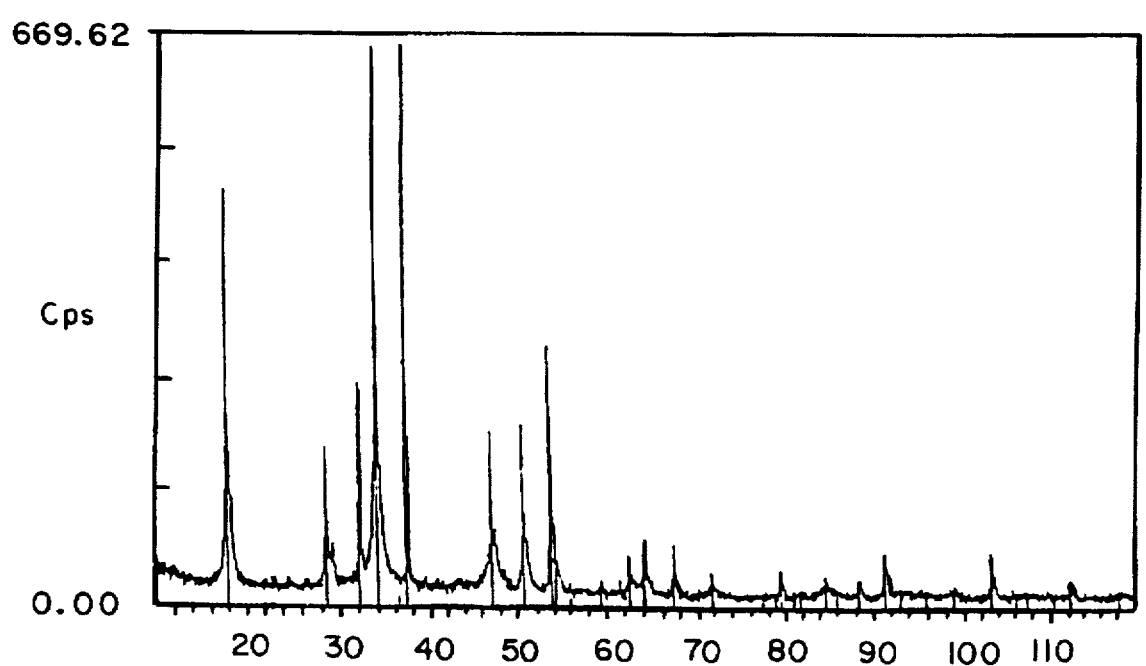
FIG. 25 is an X-ray diffraction pattern of the product of Example 9, indicating that the phase formed was CaO.

Oxide Ceramics: 5–10 micron powders of calcium carbonate were fed into the thermal reactor with argon (at 2.5 ft³/min). The reactor was inductively heated with 16 kW of RF plasma to over 5,000K in the plasma zone and about 2,500K in the extended reactor zone adjacent the converging portion of the nozzle. The vaporized stream was quenched by thermal expansion to about 100 Torr. The pressure drop across the nozzle was 250 Torr, but useful results were obtained at different pressure drops, ranging from 50 to 550 Torr. The powder produced was separated from the gas by means of a cooled copper-coil-based impact filter followed by a screen filter. FIG. 24 is the TEM image of powder produced by the invention, showing it to be in the 5 to 20 nanometer range. As expected from the calcination reaction occurring in the reactor, the XRD data (shown in FIG. 25) established that the main phase of the nanopowder was CaO. Some other phases, such as $Ca(OH)_2$, were also present due to exposure to atmospheric moisture. The size distribution of the CaO was narrow, with a mean size of about 14.8 nm and standard deviation of about 3.8 nm.

An alternate run was made with $MgCO_3$ powders with mean size of about 7 microns processed with argon. Once again, nanoscale powders of MgO were produced as evidenced by TEM and XRD data. The final product powder size was observed to vary with changes in the pressure, temperature, flow rate, and compositions.

These examples demonstrate the feasibility and effectiveness of the principles of this invention in producing nanosize powders from micron-sized precursors. The process and apparatus of the invention, utilizing ultra-rapid quenching as the process step for the formation of nanopowders, provide a practical method for controlling the size of the product by manipulating process parameters. In particular, by affecting the quenching rate by changing the pressure drop over the expansion nozzle of the invention, we found that predetermined particle sizes and size distributions can be produced reliably in a continuous, steady state process, which is easily scaleable for commercial bulk production. The process was proven viable for metals, alloys, intermetallics, ceramics, composites, and combinations thereof; the process that can also utilize feeds of reactive components and produce submicron powders of the thermodynamically stable or metastable product species at high temperatures; it is suitable for recycling and reusing product gases as feed gases; for recycling and reusing any unseparated product powders as feed material. The method and apparatus of the invention solve many problems encountered with existing processes to produce submicron powders in general and nanosize powders in particular; the process and apparatus are scaleable; the process is solvent free and therefore inherently non-polluting and of low cost; it is flexible in relation to processing different feed materials; it allows simple control of product powder size and size distribution; and it does not utilize contaminating components in the feed or for processing, therefore yielding product powders that are as pure as the powders fed to the process.

Inasmuch as one of the primary inventive concepts of the invention is the effective thermal quenching and the attendant advantages produced by ultra-rapid expansion of a vaporized suspension of the feed material, it is clear that the concept could be applied as well to a system where the precursor material is in the form of a mass evaporated by any method in a low-pressure gas. Similarly, it is expected that specific changes in materials and procedures may be made by one skilled in the art to produce equivalent results.

While the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What we claim is:

1. A method of quenching a high-temperature vapor of a precursor material to produce a nanoscale powder thereof, comprising the following steps:
   (a) producing a vapor stream of said high-temperature vapor from an inlet zone having an inlet pressure and passing said vapor stream through a convergent means to channel the vapor stream into a flow restriction having a cross-section;
   (b) quenching the vapor stream by channeling the vapor stream out of said flow restriction through divergent means to an outlet zone having an outlet pressure which is smaller than said inlet pressure; and
   (c) maintaining said inlet and outlet pressures, thereby creating a pressure differential therebetween;
   wherein said pressure differential and said cross-section of the flow restriction are adapted to produce a supersonic flow of said vapor stream.

2. The method of claim 1, wherein said pressure differential in the quenching step is sufficient to cause a temperature of the vapor/gas mixture to change at a rate of at least 1,000° C. per second.

3. The method of claim 1, further comprising the step of providing a gaseous boundary-layer stream to form a blanket over an internal surface of the convergent means.

4. The method according to claim 1, further comprising the step of cooling the convergent means, the flow restriction, and the divergent means as the vapor stream is passed from the convergent means to the divergent means.

5. The method according to claim 4, wherein the cooling step comprises providing a cooling stream around at least part of the convergent means, the flow restriction, and the divergent means.

6. The method according to claim 1, further comprising the step of collecting nanoscale of substantially the same chemical composition as the precursor material from the quenched vapor stream.

7. The method according to claim 6, wherein the collecting step comprises:
   filtering the nanoscale powder from the quenched vapor stream using a filter; and
   harvesting the nanoscale powder from the filter.

8. The method according to claim 1, further comprising, before the producing step, the step of creating the high-temperature vapor of the precursor material by (i) combining a feed stream of the precursor material with a feed stream of gas, and (ii) heating the combined feed streams of precursor material and gas to a temperature sufficient to evaporate at least some of the precursor material in the gas.

9. The method according to claim 8, wherein the combined feed streams of precursor material and gas are heated in a thermal reactor; and
   wherein interior walls of the thermal reactor are coated, at least in part, with the precursor material prior to the heating step.

10. The method according to claim 1, wherein the pressure differential is sufficient to quench the vapor stream at a rate of at least 1,000,000° C. per second.

11. The method according to claim 1, further comprising the step of passing the vapor stream through a nucleation zone prior to passing the vapor stream through the convergent means, the nucleation zone having thermokinetic conditions which favor nucleation of precursor powder from the vapor stream;
   wherein the vapor stream is passed from the nucleation zone through the convergent means as soon as nucleation of the vapor stream begins.

12. The method according to claim 11, wherein the thermokinetic conditions include a supersaturation ratio of the precursor in the vapor stream.

13. The method according to claim 11, wherein the thermokinetic conditions determined by calculating a critical cluster size required to initiate nucleation.

14. The method according to claim 14, wherein the convergent means, the flow restriction, and the divergent means comprise a Joule-Thompson converging-diverging nozzle.

15. The method according to claim 14, wherein the convergent means decreases at a convergent angle continuously from an initial cross-section to the cross-section of the flow restriction; and
   wherein the divergent means has a cross-section that increases at a divergent angle continuously from the cross-section of the flow restriction.

16. The method according to claim 1 comprising varying the rate at which the vapor stream is quenched by varying the rate at which the vapor stream expands in the divergent means.

17. The method according to claim 1, wherein the vapor stream expands supersonically in the divergent means thereby quenching the vapor stream and producing a nanoscale powder.

* * * * *

UNITED STATES PATENT AND TRADEMARK OFFICE
CERTIFICATE OF CORRECTION

PATENT NO : 5,788,738
DATED : August 4, 1998
INVENTOR(S): Pirzada, et al.

It is certified that error appears in the above-identified patent and that said Letters Patent is hereby corrected as shown below:

Column 5, Line 34; after "was", please delete "$MO_2N$" and insert therefor --$Mo_2N$--.

Column 13, line 40; after "nanosize", please delete "$MO_2N$" and insert therefor --$Mo_2N$--.

Column 13, line 60; after "was" (line 59), please delete "$MO_2N$" and insert therefor --$Mo_2N$--.

Column 16, line 43, after "claim", please delete "14" and insert therefor --1--. (Claim 14)

Signed and Sealed this

Twenty-fifth Day of May, 1999

*Attest:*

*Attesting Officer*

Q. TODD DICKINSON

*Acting Commissioner of Patents and Trademarks*